United States Patent [19]
Yen

[11] Patent Number: 5,468,741
[45] Date of Patent: Nov. 21, 1995

[54] USE OF LOW LEVELS OF MIFEPRISTONE TO TREAT LEIOMYOMATA

[75] Inventor: Samuel S. C. Yen, La Jolla, Calif.

[73] Assignee: The Regents of the University of California, Oakland, Calif.

[21] Appl. No.: 68,554

[22] Filed: May 28, 1993

[51] Int. Cl.$^6$ ................................................. A61K 31/56
[52] U.S. Cl. ........................................... 514/179; 514/967
[58] Field of Search ..................................... 514/179, 967

[56] References Cited

U.S. PATENT DOCUMENTS 5,089,488  2/1992  Ottow et al. ............................ 514/179

OTHER PUBLICATIONS

Garzo, V. G., et al., "Effects of an Antiprogesterone (RU486) on the Hypothalamic–Hypophyseal–Ovarian–Endometrial Axis During the Luteal Phase of the Menstrual Cycle", *Journal of Clinical Endocrinology and Metabolism*, vol. 66, No. 3, 508–517 (1988).

Murphy, A. A., et al., "Regression of Uterine Leiomyomata in Response to the Antiprogesterone RU 486", *Journal of Clinical Endocrinology and Metabolism*. vol. 76, No. 2, 513–517 (1993).

Primary Examiner—Kimberly R. Jordan
Attorney, Agent, or Firm—Townsend and Townsend and Crew

[57] ABSTRACT

This invention provides for novel unit doses of mifepristone to treat leiomyomata. Compared to unit dosages taught by the prior art, the claimed dosages are low and surprisingly effective. Furthermore, because higher dosages had undesired side effects, the prior art suggested that mifepristone was not suitable for long term clinical uses which are needed to treat leiomyomata. The advantages of this invention include a reduction of surgical morbidity, circumvent the need of a hysterectomy, and cost-effectiveness.

10 Claims, 4 Drawing Sheets

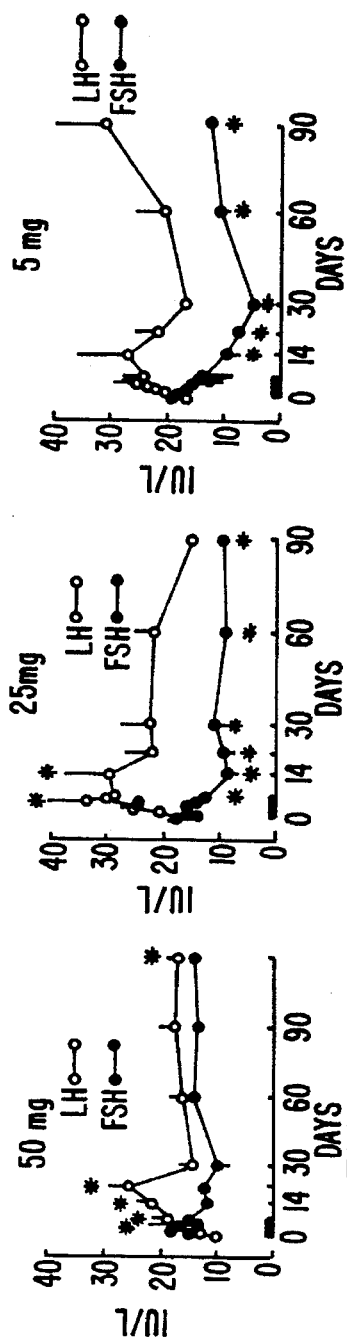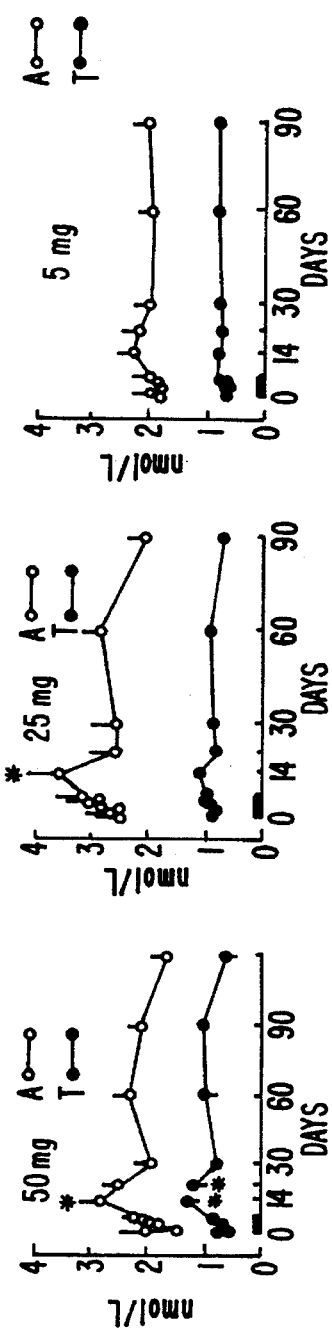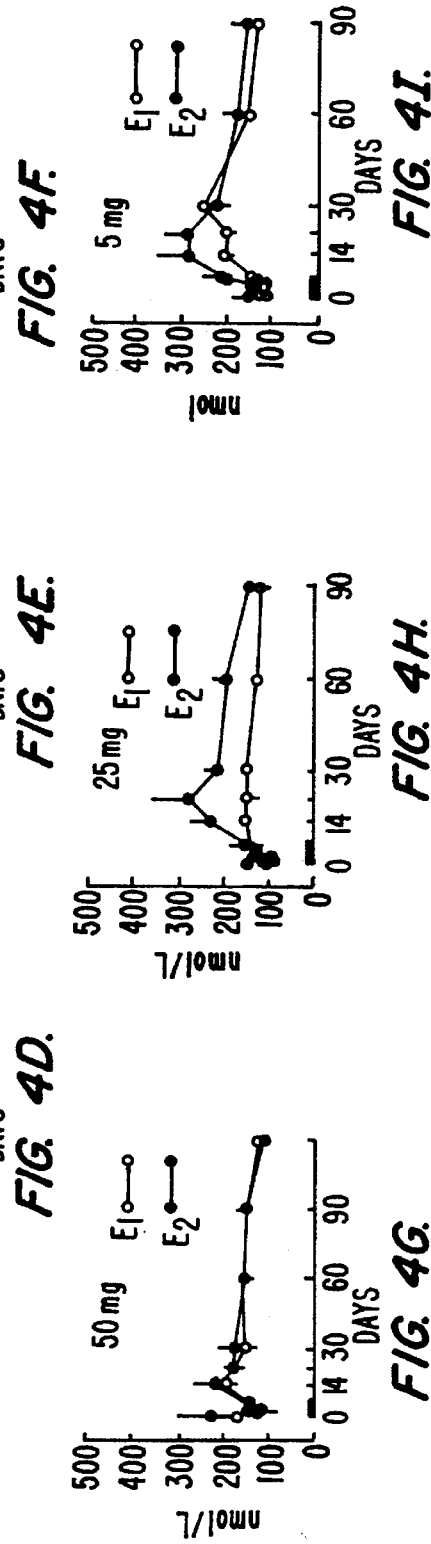

5,468,741

USE OF LOW LEVELS OF MIFEPRISTONE TO TREAT LEIOMYOMATA

BACKGROUND OF THE INVENTION

This invention provides for novel unit doses of mifepristone to treat leiomyomata. Compared to unit dosages taught by the prior art, the claimed dosages are low and surprisingly effective. Furthermore, because higher dosages had undesired side effects, the prior art suggested that mifepristone was not suitable for long term clinical uses which are needed to treat leiomyomata. The advantages of this invention include a reduction of surgical morbidity, circumvent the need of a hysterectomy, and cost-effectiveness.

Leiomyomata are common pelvic fibroid tumors occurring in up to 20% of women over 30 years of age. Leiomyomata represent one of the most frequent indications of operative procedures in woman of reproductive age. Symptoms are reported in twenty to fifty percent of cases of leiomyomata. Symptoms include pelvic pain, excessive duration or amount of menstruation, infertility and pelvic masses.

Although the mechanisms of tumorigenesis are unknown, evidence suggests that leiomyomata are ovarian steroid dependent, Buttram, V. C., et al. (1981), *Fertil. Steril.*, 36:433, incorporated herein by reference. Estrogen and growth hormone are thought to act synergistically to stimulate leiomyomata growth as the two are elevated during pregnancy when the growth of leiomyomata is rapid. That progesterone may play a role in Leiomyomata growth is suggested by the finding of increased mitotic count in leiomyomata obtained during the secretory phase than in proliferative phase of the menstrual cycle; Kawaguchi, et al. (1988) *Am. J. Obstet. Gynecol.*, 160:637. Additionally, when the GnRH-agonist and a progesterone were co-administered, the expected regression of leiomyomata size seen with GnRH-agonist alone is not achieved, Friedman et al (1988) *Fertil. Steril.* 49:404. Wilson, E. R., et al. (1980) *Obstet. Gynecol.*, 55:22 and Soules, M. R., et al. (1982) *Am. J. Obstet. Gynecol.*, 143:6 have identified receptors for both estrogen (ER) and progesterone (PR) leiomyomata tissue.

The administration of gonadotropin releasing hormone (GnRH) agonists such as leuprolide, Schlaff, W. D., et al. (1989) *Obstet. Gynecol.*, 74:857, Friedman, A. J., et al. (1987) *Fertil. Steril.*, 48:560, Friedman, A. J., et al. (1991) *Obstet. Gynecol.*, 77:720, goserelin, West, C. P., et al. (1987) *Fertil. Steril.*, 48:45, and nafarelin, Andreyko, J. L., et al. (1988) *Am. J. Obstet. Gynecol.*, 158:903, results in hypooestrogenism and causes reductions in the size of the fibroids. Unfortunately, GnRH agonist treatment cannot be continued indefinitely because of the associated vasomotor symptoms and adverse influence on bone mass. After cessation of treatment, the fibroids return to their original size within six months.

Mifepristone is a synthetic steroid with both antiprogesterone and antiglucocorticoid activities. The contragestational properties and clinical applications of mifepristone has been reviewed by Baulieu, E. E., (1989) *Science* 245:1351, and is incorporated herein by reference.

The antiglucocorticoid activity of mifepristone results in deleterious side effects glucocorticoid deprivation in the tissue and the pituitary gland resulting in an increase in serum ACTH and cortisol, as well as overt symptoms including complaints of anorexia, nausea, dizziness, weakness and somnolence.

SUMMARY OF THE INVENTION

The current invention discloses methods for treating leiomyomata with mifepristone at doses that avoid adverse side effects due to antiglucocorticoid activity.

More specifically, this invention provides for methods of treating leiomyomata in women comprising the administration of a daily unit dosage of between 0.1 to 0.6 mg mifepristone per kilogram of body weight said amount effective to alleviate the symptoms of uterine leiomyomata without clinically significant antiglucocorticoid activity and with the proviso that the total dosage does not exceed 30 mg per day. Preferred daily dosage units are between about 0.2 to about 0.4 mg mifepristone. Preferred modes of administrations are single oral dose given daily. Vaginal and transdermal routes of administration are also described. Duration of treatment is from 12 to over 52 weeks and a maintenance regimen of less than half the initial dose may be used.

BRIEF DESCRIPTION OF THE FIGURES

FIG. 4: Comparison gonadotropin, androgen and estrogen levels in normal cycling patients with leiomyomata during 3 months of RU486 treatment at 50 mg, 25 mg and 5 mg daily doses. * $P<0.005$ (LH), $P<0.0001$ (A and T), $P<0.01$ (FSH).

INTRODUCTION

Figure 1A:
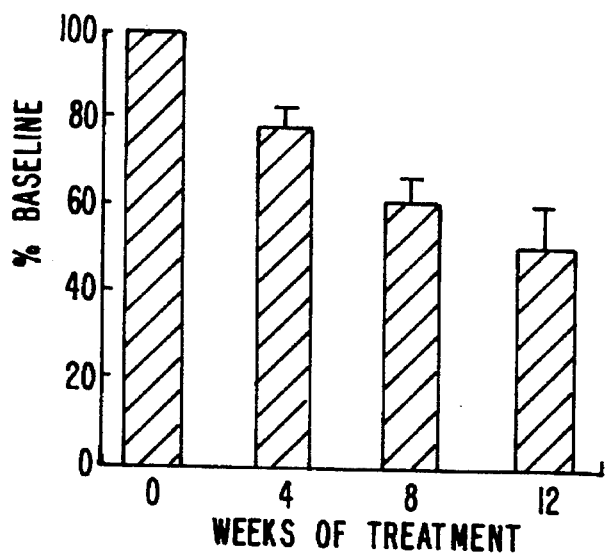
FIG. 1: Percent change in uterine leiomyomata volume in response to a 50 mg daily dose for 3 months of mifepristone treatment. Insert: Individual patient responses. * $p<0.001$.

This invention provides for the long term use of mifepristone [RU 486] to treat leiomyomata at previously undisclosed low doses. The invention is advantageous over the prior art because the prolonged use of the recited low doses of mifepristone results in dramatic improvements in the patient's condition without clinically adverse side effects due to antiglucocorticoid activity. Glucocorticoids are important regulators of intracellular metabolism. Mifepristone will bind to glucocorticoid receptors in the tissues and the pituitary gland and induce decreases in glucocorticoid effects. Such undesired activity produces increases over pretreatment levels in serum adrenocorticotropic hormone (ACTH), and cortisol levels (FIG. 1) or increased free cortisol levels measured in urine samples over a 24 hour period. Methods for assaying cortisol and ACTH are well known. Suitable immunoassays for measuring cortisol and ACTH can be found in Nicholson et al. *Clin. Chem.* 30:259, 1984 and Judd et al. *J. Clin. Endocrinol. and Metab.* 38:134, 1973, respectively. Clinically, overt symptoms of glucocorticoid deprivation include complaints of anorexia, nausea, dizziness, weakness, and somnolence.

Mifepristone pharmacology

Mifepristone (11β-(4-dimethyl-amino phenyl)-17β-hydroxy- 17α(prop-1-ynyl)-estra-4,9-dien-3-one) is a 19-nonsteroid, lacking the C19-methyl group of natural progesterone (P) and glucocorticosteroids (G). The drug has been found to have a high affinity for both the progesterone receptor (PR) and the glucocorticosteroid receptor (GR) and has strong antiprogesterone and antiglucocorticosteroid activity.

In many countries, mifepristone is used as an abortifacient. It is considered clinically safe in relatively high doses for short periods of time. Because of its antiprogesterone activity, it has been evaluated for alternative medical uses including treatment of uterine leiomyomata. Previous reports have indicated efficacy at levels which are accompanied by undesirable side effects. These side effects are of a nature which made the long term use of mifepristone contraindicated.

Mifepristone is administered orally in capsule or in tablet form. It can also be delivered by transdermal or via injection of microsperes associated with mifepristone slowly released subcutaneously. Both routes afford constant delivery for weeks or months. For a brief review of present methods for drug delivery, see, Langer, *Science* 249:1527–1533 (1990), which is incorporated herein by reference. Methods for preparing administrable compounds are known or are apparent to those skilled in the art and are described in more detail in, for example, Remington's *Pharmaceutical Science,* 17th ed., Mack Publishing Company, Easton, Pa. (1985), which is incorporated herein by reference, and which is hereinafter referred to as "Remington."

For solid compositions, conventional nontoxic solid carriers may be used which include, for example, pharmaceutical grades of mannitol, lactose, starch, magnesium stearate, sodium saccharine, talcum, cellulose, glucose, sucrose, magnesium, carbonate, and the like. For oral administration, a pharmaceutically acceptable nontoxic composition is formed by incorporating any of the normally employed excipients, such as those carriers previously listed.

Oral solid dosage forms are preferentially compressed tablets or capsules. Compressed tablets may contain any of the excipients described above which are diluents to increase the bulk of the mifepristone so that production of a compressed tablet of practical size is possible. Binders, which are agents which impart cohesive qualities to powdered materials are also necessary. Starch, gelatin, sugars such as lactose or dextrose, and natural and synthetic gums are used. Disintegrants are necessary in the tablets to facilitate breakup of the tablet. Disintegrants include starches, clays, celluloses, algins, gums and crosslinked polymers. Lastly small amounts of materials known as lubricants and glidants are included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants. Procedures for the production and manufacture of compressed tablets are well known by those skilled in the art (See Remington).

Capsules are solid dosage forms using preferentially either a hard or soft gelatin shell as a container for the mixture of RU486 and inert ingredients. Procedures for production and manufacture of hard gelatin and soft elastic capsules are well known in the art (See Remington).

For parenteral administration, fluid unit dosage forms are prepared utilizing the compounds and a sterile vehicle, water being preferred. The mifepristone, depending on the vehicle and concentration used, can be either suspended or dissolved in the vehicle. In preparing solutions the compound can be dissolved in water for injection and filtered sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compounds are suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of mifepristone.

Additionally, a suppository can be employed to deliver the mifepristone. The active compound can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate. These suppositories can weigh from about 1 to 2.5 gm.

Transdermal delivery systems comprising a penetration enhancer and an occlusive backing are of use to deliver mifepristone. Examples of penetration enhancers include dimethyl sulfoxide, dimethyl acetamide and dimethylformamide.

Implants comprising polymeric devices which slowly release or slowly erode and release within the body to provide continuous supplies of mifepristone are also of use. Implants include subcutaneous devices such as those routinely used to deliver norgestrienone or progestin R2323 and other medicaments. Other implants include intravaginal and intrauterine devices.

The implants may be made polymers which generally comprise but are not limited to non-toxic hydrogels, silicones, polyethylenes, ethylene-vinyl acetate copolymers and other biodegradable polymers. Hydrogels include polyhydroxyalkyl methacrylates, polyacrylamide and polymethacrylamide, polyvinylpyrrolidone and polyvinyl alcohol. A preferred silicone is polydimethylsiloxane. Biodegradable polymers include polylactic acid [PLA], polyglycolic acid [PGA], copolymers of PLA and PGA, and polyamides.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. Examples of suitable unit dosage forms in accord with this invention are tablets, capsules, pills, suppositories, powder packets, wafers, granules, cachets, teaspoonfuls, tablespoonfuls, dropperfuls, ampoules, vials, aerosols with metered discharges, segregated multiples of any of the foregoing, and other forms as herein described. It being understood that implants will have a capacity in excess of the daily unit dosage and that in such a context, the unit dosage is defined by the amount of active compound released by the implant on a daily basis.

In calculating the dosage for individuals one has to take into consideration the weight of the individual and the mode of administration. The following guidelines provide levels of mifepristone which are clinically effective but produce no significant side effects due to antiglucocorticoid activity. Presuming an average weight of 120 pounds or 53 kilograms, the daily unit dosage of mifepristone is between 0.1 mg to 0.6 mg with the proviso that total dosage for an individual not exceed 25 mg of mifepristone per day. Preferred oral doses are between 0.2 and 0.4 mg daily. Other routes of administration can be in comparison with oral routes using blood levels to provide clinical success. Once the leiomyomata tumors have fully responded, a maintenance dosage of around 5 mg can be administered over a long period, e.g., in excess of 12 months.

Determining patient response in the treatment of leiomyomata

Changes in tumor volume are determined by way of pelvic sonogram examinations. Each tumor is measured in three dimensions. The sonograms are given prior to administration of mifepristone and monthly thereafter. The sonogram can be performed either vaginally and/or abdominally. Complete blood counts and chemistry panels are made on blood samples taken before drug treatment and monthly during treatment.

Serum samples for hormonal evaluation are obtained before and after initiation of therapy, daily for one week, weekly for 4 weeks and monthly thereafter. Serum concentrations of luteinizing hormone (LH), follicle-stimulating hormone (FSH), prolactin (PRL), thyroid-stimulating hormone (TSH), estradiol ($E_2$), estrone ($E_1$) testosterone (T), dehydroepiandrosterone (DHEA) androstenedione (A), progesterone, cortisol and plasma adrenocorticotropic hormone (ACTH), dehydroepiandrosterone sulfate (DHEAS), testosterone (T), thyroid stimulating hormone (TSH) and prolactin (PRL) are determined by radioimmunoassay. The following references describe these procedures which are routine assays. Anderson, D. C., et al. (1976), Anderson, D. C., et al. (1976), *Steroids*, 28:179–183; Yen et al., *J. Clin Endocrinol. and Metab.*, 30:325 (1970); Yen et al., *J. Clin Endocrinol. and Metab.* (1968) 28:1763; Nicholson et al., *Clin. Chem.* (1984) 30:259; Judd et al., *J. Clin. Endocrinol and Metab.* (1973) 38:134.

Individual tumor volumes are calculated using the formula for a sphere ($4\pi abc/3$ in $cm^3$) where a, b and c represent the radii of the sphere in 3 dimensions (Friedman, et al. (1988), *Fertil. Steril.*, 49:404–409) Significant changes in leiomyomata volume and hormone data are determined by repeated measures analysis of variance with subsequent post hoc testing (Dunnett's). The Pearson Product-Momen correlation coefficient is used to assess the power of association between two hormonal variables. Results are expressed as mean ± SE (standard error). Bone mineral density data is analyzed using a paired T-test. $P<0.05$ is considered significant.

Histology and Immunocytochemistry for Receptor Proteins

Leiomyomata and myometrial tissue are obtained at surgery from treated and untreated patients in the follicular phase of the cycle. Tissues are fixed in neutral-buffered formalin for 24 hrs and embedded in paraffin. Mounted sections (8 μm thick) are used for immunohistochemical analysis (Cheung, L., et al. (1988), *Laboratory Investigation*, 38:346; Sternfeld, M. D., et al. (1988) *Fertil. Steril.*, 49:342; Mutch, D. G., et al. (1987) *Am. J. Obstet. Gynecol.*, 157:924). Briefly, after treatment with pronase-PBS solution, sections of tissue are incubated with primary antibody (Abbott ER-CIA monoclonal or 2A09-18PR monoclonal, Abbott Laboratories, North Chicago, Ill.) for 30 hrs. Secondary antibody, biotinylated goat anti-rat IgG, is applied for 30 min, followed by tertiary antibody, streptavidin-alkaline phosphatase for 30 minutes. Samples are developed in McGrady's reagent. Pronase treatment is not required with the PR primary antibody. PR antibody is used at a 1:5 dilution. The ER antibody is not diluted. For control, a duplicate section of each slide is stained in a similar manner, except the primary antibody is eliminated.

Levels of ER and PR are evaluated by determining the distribution and intensity of the staining, and quantified using HSCORE (histochemistry score) by two investigators. The intensity of staining is assigned as 0= none, 1= weak, 2= distinct, 3= strong. The HSCORE is calculated using the followed equation: $HSCORE = \epsilon P_i(i+1)$, where i= 0, 1, 2, or 3 and $P_i$ is the percentage of stained cells for each intensity (Cheung, L., et al. (1988), *Laboratory Investigation*, 38:346). Intra-observer reliability and correlation with hormone-binding assays have been demonstrated previously (Baird, D. T., et al. (1989) *Horm. Res.*, 32:154; Collins, R. L., et al. (1986) *J. Clin. Endocrinol. Metab.*, 63:1270-6).

Levels of ER and PR are evaluated using an image analysis software "Image" (NIH program). This computer program captures an image from the microscope and provides a quantitative analysis of staining intensity. An arbitrary numerical unit is assigned to each slide and its non-immune control. For each immunostained section, the adjacent non-immune control is subtracted and the difference reported.

Statistical analysis was performed using the Student's t-test to evaluate differences in mean scores between study patients and controls for each tissue type.

Antiglucocorticosteroid affects can be demonstrated by increase in serum or urinary cortisol ($P<0.01$) and adrenocorticotropic hormone ($P<0.05$) levels.

The following example is provided by way of illustration only and not by way of limitation. Those of skill will readily recognize a variety of noncritical parameters which could be changed or modified to yield essentially similar results.

EXAMPLE ONE: Mifepristone treatment (50 mg/day) of 10 patients with uterine leiomyomata and regular menstrual cycles a) Subject Selection Ten normal cycling women between the ages of 18–45 years with symptomatic uterine leiomyomata were recruited for this study. None of the subjects had taken any hormonal medications for at least 3 months prior to the study. All subjects used barrier contraception.

b) Clinical Study

Each subject had a pelvic sonogram (ATL ultramark 4, Tempe Ariz.) performed prior to initiation of drug therapy and monthly thereafter. This was performed either vaginally and/or abdominally for each tumor measured in three dimensions.

Subjects were given mifepristone 50 mg/day for 3 months beginning on day 1–3 of the menstrual cycle. Baseline and monthly blood samples for complete blood count and chemistry panel were obtained. Serum samples for hormonal evaluations were obtained before and after initiation of therapy, daily for one week, weekly for 4 weeks and monthly thereafter. Luteinizing hormone (LH), follicle stimulating hormone (FSH), estrone ($E_1$), estradiol ($E_2$), progesterone (P), androstenedione (A), dehydroepiandrosterone (DHEA), dehydroepiandrosterone sulfate (DHEA-S), testosterone (T), cortisol (F), cortisol (F), thyroid stimulating hormone (TSH) and prolactin (PRL) were determined by radioimmunoassay. The intra-assay and inter-assay coefficients of variation (CV) were<3.5% and 10%, respectively for all hormones measured. All samples for each subject were determined in the same assay.

Bone mineral density, determined by dual photon x-ray absorptiometry of the spine and hips was performed before and at the end of therapy.

c) Data Analysis

Individual tumor volumes were calculated using the formula for a sphere ($4\pi abc/3$ in cm$^3$) where a, b, and c represent the radii of the sphere in 3 dimensions. Significant changes in leiomyomata volume and hormone data were determined by repeated measures analysis of variance with subsequent post hoc testing (Dunnett's). The Pearson Product-Moment correlation coefficient was used to assess the power of association between two hormonal variables. Results are expressed as mean± SE. Bone mineral density data was analyzed using a paired T-test. $P<0.05$ was considered significant.

d) Histology and Immunocytochemistry for Receptor Proteins

Leiomyomata and myometrial tissue were obtained at surgery from six mifepristone treated patients and six untreated patients in the follicular phase of the cycle. Tissues were fixed in neutral-buffered formalin for 24 hrs and embedded in paraffin. Mounted sections (8 μm thick) were used for immunohistochemical analysis. Briefly, after treatment with pronase-PBS solution, sections of tissue were incubated with primary antibody (Abbott ER-CIA monoclonal or 2A09-18PR monoclonal, Abbott Laboratories, North Chicago, Ill.) for 30 hrs. Secondary antibody, biotinylated goat anti-rat IgG, was applied for 30 min, followed by tertiary antibody, streptavidin-alkaline phosphatase for 30 minutes. Samples were developed in McGrady's reagent. Pronase treatment was not required with the PR primary antibody. PR antibody was used at a 1:5 dilution. The ER antibody was not diluted. For control, a duplicate section of each slide was stained in a similar manner, except the primary antibody was eliminated.

Levels of ER and PR were evaluated by determining the distribution and intensity of the staining, and quantified using HSCORE by two investigators. The intensity of staining was assigned as 0= none, 1= weak, 2= distinct, 3= strong. The HSCORE was calculated using the following equation: $HSCORE = \epsilon P_i(i+1)$, where i= 0, 1, 2, or 3 and $P_i$ is the percentage of stained cells for each intensity. Intraobserver reliability and correlation with hormone-binding assays have been demonstrated previously.

Levels of ER and PR were also evaluated using an image analysis software "image" (NIH program provided by Wayne Rasband). This computer program captures an image from the microscope and provides a quantitative analysis of staining intensity. An arbitrary numerical unit is assigned to each slide and its non-immune control. For each immunostained section, the adjacent non-immune control was subtracted and the difference reported.

Statistical analysis was performed using the Student's t-test to evaluate differences in mean scores between study patients and controls for each tissue type.

e) Results

Figure 1B:
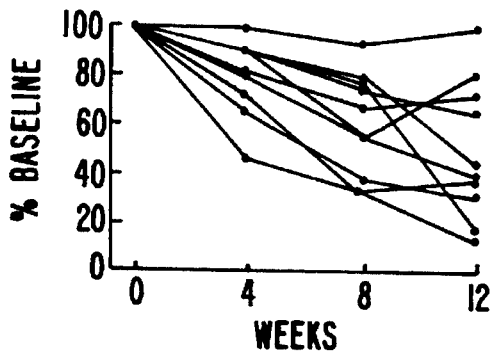

The extended (3 months) administration of mifepristone resulted in a significant decline in leiomyomata volume by the 8th ($P<0.001$) and 12th week ($P<0.001$) (FIG. 1). The individual responses varied from no change to a marked decrease of 87% from baseline but 9 of 10 patients exhibited an overall decrease in leiomyomata volume (FIG. 1 insert).

Figure 2A:
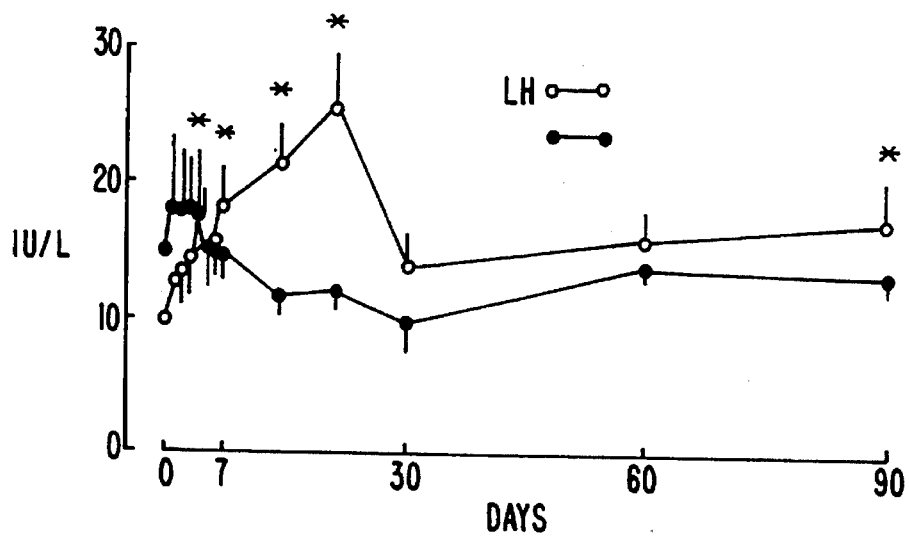
FIG. 2: Gonadotropin, androgen and estrogen levels in normal cycling patients with leiomyomata during 3 months of mifepristone treatment begun in the early follicular phase. * $p<0.005$ (LH), $p<0.001$ (A and T).
Figure 2B:
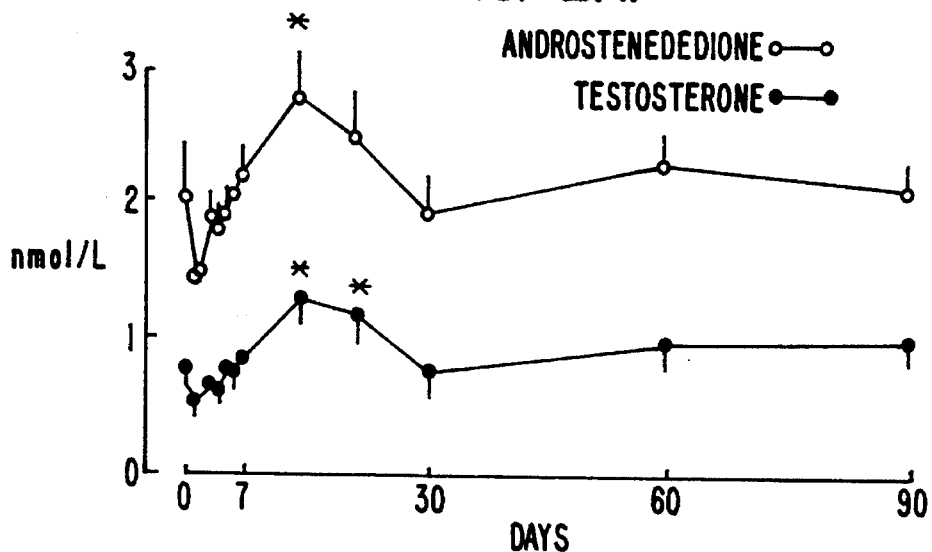
Figure 2C:
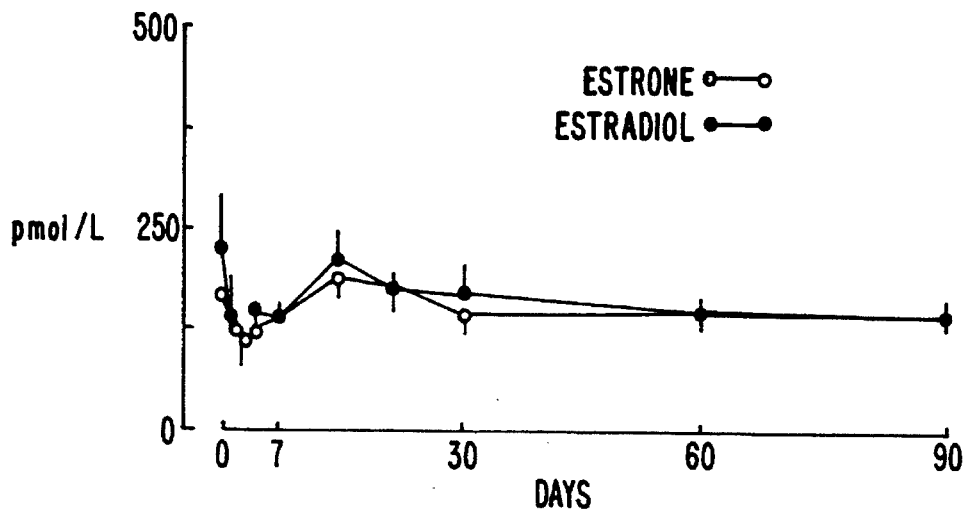

All women were amenorrheic during the course of treatment with low serum progesterone levels (<2 nmol/L). The time course of hormonal changes are shown in FIG. 2. When compared with pretreatment values, mifepristone treatment induced an increase in mean LH levels ($P<0.005$) but not FSH levels during the first three weeks and it was associated with a concomitant increase in serum A ($P<0.0001$) and T ($P<0.0001$) levels (r=0.699, $P<0.006$). These elevated levels then returned to baseline at 4 weeks and remained unchanged thereafter. There was no significant change in serum $E_1$ and $E_2$ levels in response to mifepristone treatment (FIG. 2). DHEA-S ($P<0.0001$) and cortisol ($P<0.01$) but not DHEA levels significantly increased at 12 weeks. SHBG, TSH, and PRL levels did not change significantly (Table 1). After discontinuation of mifepristone regular cycles ensued within 3–6 weeks.

No significant change in total bone mineral density of the spine (Lumbar 2–4) was noted after 3 months of treatment (1.014± 0.095 g/cm$^2$ vs. 0.910± 0.153 g/cm$^2$). Total bone mineral density of the proximal femur was not significantly different after 3 months of the treatment (0.854± 0.319 vs. 0.835± 0.173 g/cm$^2$).

Mifepristone was well tolerated by all patients. Four subjects experienced mild, atypical hot flashes which resolved during the second month of therapy. At the end of three months of treatment, one patient complained of joint pain and a transient mild increase in transaminases (AST-99 U/L; ALT-148 U/L) was noted. Mifepristone was discontinued and joint pain disappeared a few days after. Serum transaminases normalized within one month.

f) Immunohistochemistry

There was a significant decrease in PR staining in both leiomyomata and myometrium of mifepristone treated patients when compared to control (Table 2). Localization of PR was exclusively nuclear. Using image analysis, significantly ($P<0.05$) more PR immunoreactivity was seen in leiomyomata of treated or control patients when compared to their respective myometrium. No immunostaining was seen in the non-immune control sections.

The immunohistochemical analysis of ER content in myometrium and leiomyomata of mifepristone and control patients did not reveal a significant difference with HSCORE or image analysis (Table 3). With image analysis, ER immunoreactivity was significantly greater ($P<0.05$) in control leiomyomata when compared to control myometrium while no difference in ER immunoreactivity was seen between leiomyomata and myometrium of treated patients. ER immunoreactivity was localized predominantly in the nuclei, although some staining was seen in the cytoplasm of cells. Non-immune control sections show little non-specific staining.

EXAMPLE TWO: Regression of Uterine Leiomyomata to Mifepristone: Dose Response Effect Example one shows that the administration of mifepristone at 50 mg daily dose induces ovarian acyclicity and, on the average the patients had obtained, a 22% decrease in leiomyomata volume at 1 month, 40% decrease at 2 months and 50% decrease after 3 months of treatment. This example shows the effect of mifepristone on leiomyomata volume in response to two lower doses i.e. 25 mg and 5 mg.

Eight patients with symptomatic leiomyomata were placed on 25 mg of mifepristone daily for three months and seven patients were begun on 5 mg of mifepristone daily. Changes in tumor volume were measured as described in example one. Baseline ultrasound examinations were obtained and repeated monthly throughout treatment. Each fibroid was mapped and measured in 3 dimensions and followed systematically throughout treatment. Complete blood counts and chemistry, as well as hormonal evaluations were performed as described above. Treatment was initiated on cycle day 1–3. Blood samples were obtained daily for 7 days, weekly for 4 weeks and monthly for 3 months.

Figure 3:
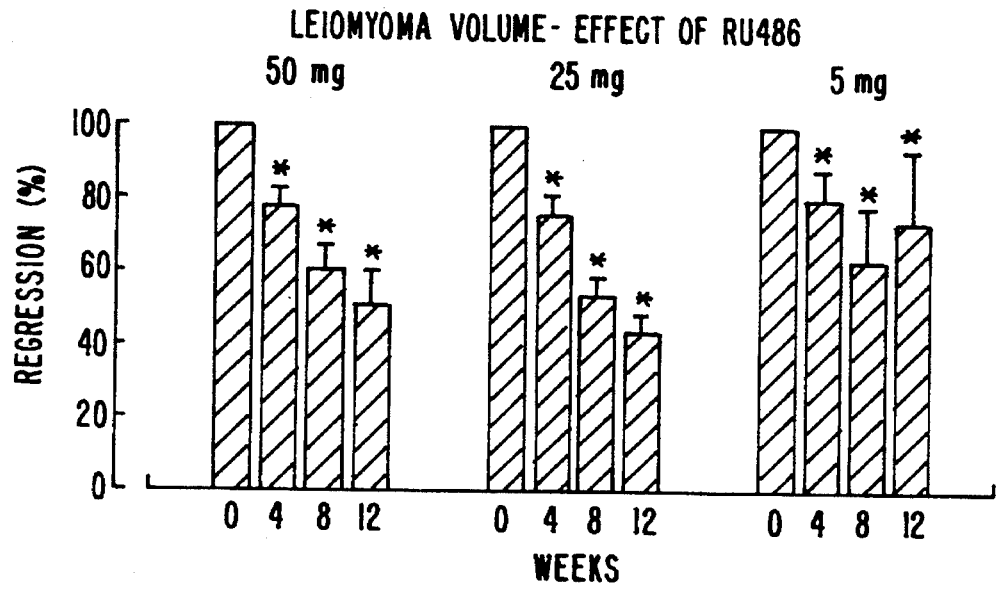
FIG. 3: Comparison of percent change in uterine leiomyoma volume in response to 3 months treatment of RU486 at daily doses of 50 mg, 25 mg and 5 mg.

All patients became amenorrheic during treatment and 5 experienced mild hot flashes. Two patients on 25 mg had mild elevations of liver transaminases which resolved within 1 month of discontinuing the medication. Regressive response of mean leiomyomata volume in patients treated with 25 mg of mifepristone daily was 21.7% at 1 month, 56.6% at 2 months and 68.4% after 3 months ($p<0.001$) and at 5 mg of mifepristone was 36.5% after the first month, 27.2% after the second month, and 29.2% after the third month of therapy ($p<0.05$). (See FIG. 3)

FIG. 4 provides the affect of 50, 25, and 5 mg doses mifepristone on LH, FSH, androstenedione (A), testosterone (T), and $E_1$ and $E_2$. At the 50 mg and 25 mg daily doses, levels of LH, androstenedione (A) and testosterone (T) increased during the first two weeks of treatment. In contrast, significant decline in FSH levels was evident in both 25 mg and 5 mg doses which lasted for the entire course of treatment. This inhibitory effect of RU486 on FSH levels, however, was not observed with 50 mg dose. In the face of decreased FSH, serum $E_2$ and $E_1$ levels were maintained in the early to mid-follicular phase range. These findings are entirely consistent with previous studies, which indicated that RU486 exerted impacts at multiple sites with diverse actions.

Figure 5:
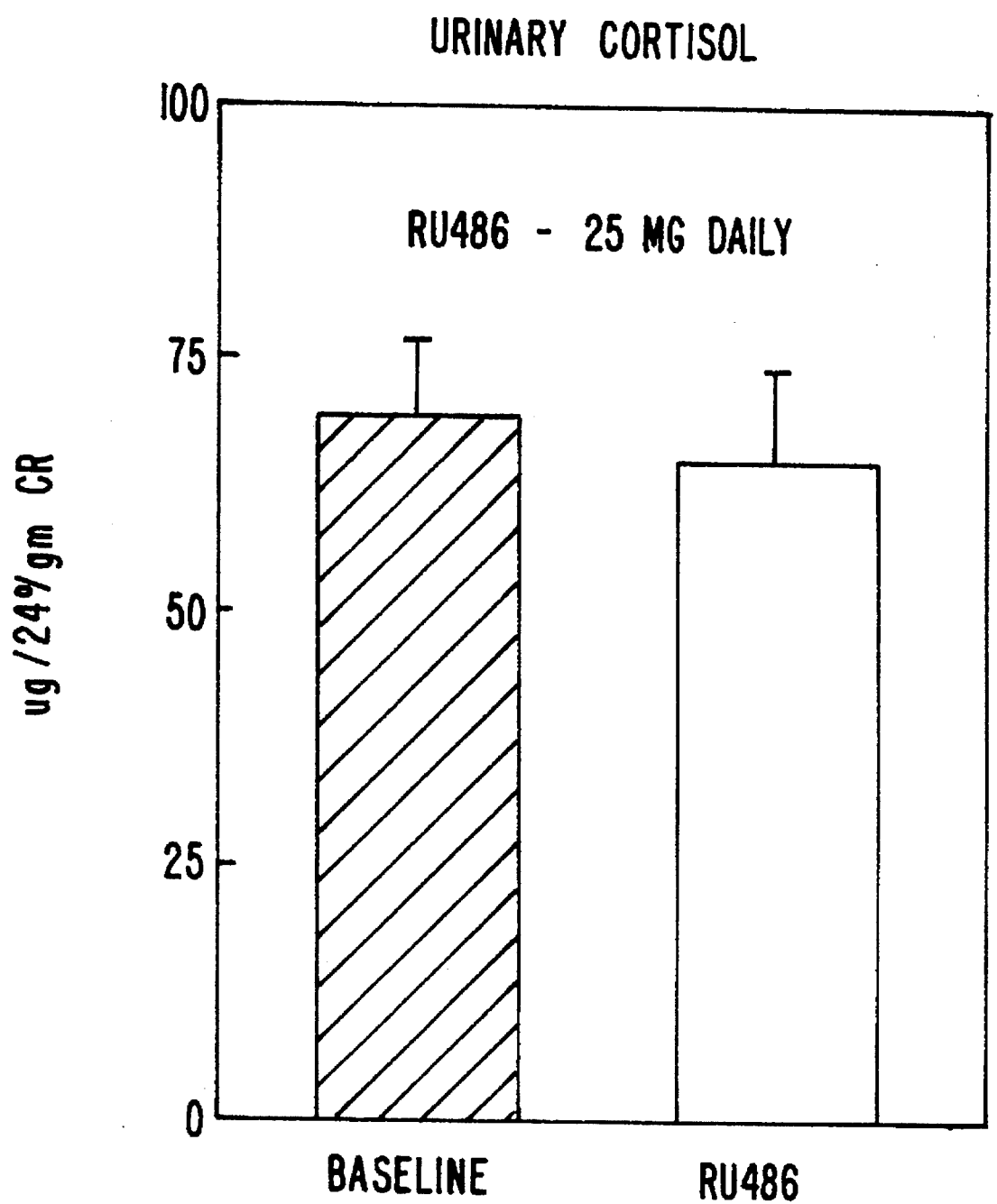
FIG. 5: Twenty-four hour urinary free cortisol levels (mean± SE) at baseline and after 3 months treatment of RU486 at 25 mg daily dose.

At both 25 mg and 5 mg daily dose, urinary free cortisol levels were unchanged (FIG. 5) and thus, the antiglucocorticoid action can be disassociated from the antiprogesterone action of RU486 at these doses.

RU486 at 25 mg dose causes a greater than 50% reduction and 5 mg dose induced a small but significant decline in myoma volume unaccompanied by antiglucocorticoid effects. These findings illustrate that long-term use of mifepristone levels of about 25 mg/day may serve as an effective and safe alternative for the management of myoma. The therapeutic strategies of a step-down dose of mifepristone will be used. At 25 mg daily dose or less, a 50% down regulation of these tumors by 3 months is anticipated. This is followed by a reduced daily dose of 5 mg to serve as a long-term (years) maintenance of regression.

TABLE 1

| HORMONE | BASELINE | 12 WEEKS | SIGNIFICANCE |
| --- | --- | --- | --- |
| DHEAS | 1.52 ± 0.30 μmol/L | 2.01 ± 0.36 μMol/L | P < .0001 |
| CORTISOL | 1653.2 ± 514.8 nmol/L | 2453.3 ± 331.1 nmol/L | P < .01 |
| DHEA | 3.75 ± 0.91 nmol/L | 5.6 ± 0.47 nmol/L | NS |
| SHGB | 74.47 ± 6.08 nmol/L | 54.35 ± 8.9 nmol/L | NS |
| TSH | 1.70 ± 0.43 μU/L | 2.23 ± 0.67 μU/L | NS |
| PRL | 32.43 ± 6.27 μg/L | 22.30 ± 7.96 μg/L | NS |

NS - not statistically significant

TABLE 2

|  |  | Progesterone Receptor | | MYOMETRIUM |
|---|---|---|---|---|
|  |  | LEIOMYOMATA | | |
|  |  | RU-486 | Control | RU-486 Control |
| Progesterone | HSCORE | 2.50 ± 0.36 | 3.5 ± 0.39[a] | 2.40 ± 0.433.57 ± 0.73[c] |
| Receptor | IMAGE | 22.56 ± 5.92 | 36.92 ± 8.28[b] | 15.51 ± 3.424.67 ± 7.17[d] |

[a] $p < .001$ vs leiomyomata RU-486
[b] $p < .01$ vs leiomyomata RU-486; $p < .05$ vs myometrium control
[c] $p < .05$ vs myometrium RU-486
[d] $p < .05$ vs myometrium RU-486; $p < .05$ vs leiomyomata control

TABLE 3

|  |  | Estrogen Receptor | | MYOMETRIUM |
|---|---|---|---|---|
|  |  | LEIOMYOMATA | | |
|  |  | RU-486 | Control | RU-486 Control |
| Esterone | HSCORE | 3.30 ± 0.31 | 3.40 ± 0.19 | 3.33 ± 0.303.50 ± 0.27 |
| Receptor | IMAGE | 18.09 ± 3.83 | 23.08 ± 4.25[e] | 17.42 ± 3.9817.61 ± 2.91 |

[e] $p < .05$ vs myometrium control

What is claimed is:

1. A method for treating leiomyomata in women comprising the administration of a daily unit dosage of between 0.1 to 0.6 mg mifepristone per kilogram of body weight said amount effective to alleviate the symptoms of uterine leiomyomata without clinically significant antiglucocorticoid activity and with the proviso that the total dosage does not exceed 25 mg per day.

2. A method of claim 1 wherein the unit dosage is between 0.2 and 0.4 mg mifepristone.

3. A method of claim 1 wherein the administration is once daily.

4. A method of claim 1 wherein the mode of administration is oral.

5. A method of claim 1 wherein the mode of administration is vaginal.

6. A method of claim 1 wherein the mode of administration is transdermal.

7. A method of claim 1 wherein the mifepristone is in a tablet form.

8. A method of claim 1 wherein the duration of treatment is between 4 weeks and 36 weeks.

9. A method of claim 1 wherein the duration of treatment is between 8 weeks and 24 weeks.

10. A method of claim 1 further comprising a period of treatment during which a daily unit dosage of mifepristone is administered, wherein said dosage is administered at less than one half the initial treatment daily unit dosage.

* * * * *